United States Patent [19]

Lapicola

[11] Patent Number: 4,968,629
[45] Date of Patent: Nov. 6, 1990

[54] BLOOD DILUENT FOR AUTOMATIC AND SEMI-AUTOMATIC DETERMINATION OF WHITE CELLS AND METHOD OF UTILIZING SAME

[75] Inventor: James D. Lapicola, Martinez, Calif.

[73] Assignee: Hematology Marketing Associates, Inc., Plano, Tex.

[21] Appl. No.: 133,028

[22] Filed: Dec. 16, 1987

Related U.S. Application Data

[63] Continuation of Ser. No. 898,256, Aug. 20, 1986, abandoned.

[51] Int. Cl.$^5$ .............................................. G01N 31/00
[52] U.S. Cl. ........................................ 436/18; 436/17; 436/8; 252/408.1
[58] Field of Search ...................................... 436/8–18; 252/408.1

[56] References Cited

U.S. PATENT DOCUMENTS

| | | | |
|---|---|---|---|
| 3,962,125 | 6/1976 | Armstrong | 436/10 |
| 4,102,810 | 7/1978 | Armstrong | 436/10 |
| 4,213,876 | 7/1980 | Crews et al. | 436/18 |
| 4,506,018 | 3/1985 | North, Jr. | 436/10 |
| 4,529,705 | 7/1985 | Larsen | 436/10 |
| 4,617,275 | 10/1986 | Matsuda et al. | 436/10 |

*Primary Examiner*—Robert A. Wax
*Assistant Examiner*—T. J. Wallen
*Attorney, Agent, or Firm*—Kokjer, Kircher, Bradley, Wharton, Bowman & Johnson

[57] ABSTRACT

A universal blood diluent for use in hematology analysis is the subject of this invention. The diluent consists of an aqueous solution of 0.4–1.5% by weight of either $Na_2SO_4$ or $NaNO_3$ or a combination of the two. Also included is 0.1–0.4% by weight of a salt of the formula $XH_2PO_4$ where X is either Na or K and 0.1–2.4% by weight of a salt of the formula $X_2HPO$ where X is Na or K. The phosphate salts may be hydrous or anhydrous. A mixture of Na and K phosphate salts may also been employed. The salts should be present in a ratio of from 1:1 to 1:6 (by weight), $XH_2PO_4:X_2HPO_4$. 0.1 to 1% by weight of one or both of NaCl and KCl is also included. The $Na_2SO_4$ and $NaNO_3$ should be present in a ratio of at least 1:1 (by weight) relative to the chloride salt. The pH of the diluent should be within the range of 6.0–8.0 and it should have an osmotic strength of 200–400 milliosmoles. The diluent may be used in either automated or semi-automated analytical equipment. The use of an inorganic buffer offers numerous advantages over prior art organic buffers including cost an better performance. The diluent allows for leukocyte analysis as well as maintaining erythrocyte morphology until a lysing reagent is introduced.

11 Claims, No Drawings

BLOOD DILUENT FOR AUTOMATIC AND SEMI-AUTOMATIC DETERMINATION OF WHITE CELLS AND METHOD OF UTILIZING SAME

This is a continuation of application Ser. No. 898,256, filed Aug. 20, 1986, now abandoned.

BACKGROUND OF THE INVENTION

This invention relates generally to a blood diluent and more particularly to a diluent that can be utilized in both automatic and semi-automatic systems for determining white blood cell populations, including two or more sub-populations of leukocytes.

Probably the most universally used medical diagnostic laboratory procedure is to analyze the blood of a patient for the purposes of determining the overall health of the patient as well as identifying specific intrusions into the body of an undesired nature. Two of the more important parameters studied in hematology analysis are red blood cell counts (erythrocytes) and white blood cell counts (leukocytes). The ability to differentiate sub-populations among the leukocyte group has become possible with recent advances in technology and is a particularly useful analytical tool.

Procedures for obtaining white blood cell counts vary from semi-automated procedures where preparatory steps are done manually prior to the actual counting done by single transducers, to completely automated procedures which employ sophisticated electronic circuitry capable of determining the form and size of a particular particle (i.e., cell) passing through a defined electrical field. U.S. Pat. No. 3,549,994 discloses an automated machine for hematology analysis and discusses the various factors to be considered in providing an automated system.

It has long been known that employing an aqueous solution of chemical salts will provide an electrolyte solution capable of conducting current to which a blood sample can be added for the purpose of diluting the erythrocytes and leukocytes as well as other blood components so as to enable the desired parameters to be observed, measured and counted. The general requirements for an effective diluent are: that it be capable of conducting an electric current; that it should stabilize the red blood cells enabling their volume to be unaltered and accurately measured; that it be nonreactive and have no adverse affect on white blood cells; and that it not interfere in any way with the conversion of hemoglobin to the cyanmethemoglobin form in which hemoglobin is best measured.

U.S. Pat. No. 3,962,125 discloses a multipurpose diluent for use in automated analytical equipment of the type broadly discussed above. The diluent disclosed in the reference patent includes inorganic salts, an organic chelating agent and a bacteriostat.

Another diluent of the prior art is disclosed in U.S. Pat. No. 4,346,018. The formulation set forth in this patent includes a mixture of organic salts, chelating agents, stabilizers and bacteriostats.

An improvement in lysing agents is the subject of U.S. Pat. No. 4,485,175. The system employed in this patent provides for a modified exposure of leukocytes which enables one to obtain a total of three populations, namely, lymphocytes, monocytes and granulocytes. According to the teachings of U.S. Pat. No. 4,485,175, it is necessary to employ a relatively expensive organic buffer in the diluent for use with the lysing agent disclosed in this patent in order to obtain the improved three leukocyte sub-populations.

The diluents of both the '018 and '175 patents discussed above require the use of cell stabilizers in order to maintain the integrity of the cells for a sufficient length of time to be counted and sized.

U.S. Pat. No. 4,213,876 sets forth a formulation for a novel diluent which utilizes a combination of inorganic salts sodium chloride, sodium dihydrogen phosphate and disodium phosphate, plus sodium sulfate anhydrous. The diluent set forth in this patent also includes, however, a combination of 8-hydroxyquinoline and procaine hydrochloride anhydrous which was found to be superior in terms of its stability and ability to suppress bubbles which have sometimes been a problem when bacteriostats are included in the formulation.

SUMMARY OF THE INVENTION

The present invention relates to a diluent and method for subjecting a whole blood sample to analysis for erythrocyte, leukocyte and platelet count and size, and the determination of hemoglobin concentration (depending on lysate used). The system employs a novel buffer of inorganic salts which, in the particular combination specified, allows the same diluent to be utilized in obtaining subpopulations of leukocytes or a single leukocyte population while maintaining erythrocyte stability. In broadest form the invention comprises a diluent including one or more of $Na_2SO_4$ and $NaNO_3$ in combination with sodium or potassium phosphate monobasic and disodium or dipotassium hydrogen phosphate. Up to fifty percent of the quantity of sodium sulfate and sodium nitrate can be replaced with less expensive sodium or potassium chloride. A bacteriostat may also be included in the formulation. Various lysing agents can be utilized, but when sub-populations of leukocytes are desired, the lysing agent should consist of one or more quarternary ammonium salts.

OBJECTS OF THE INVENTION

An important objective of this invention is to provide a universal diluent which can be utilized in blood cell analysis of either a semi-automated or fully automated nature.

Another objective of this invention is to provide a diluent for use in hematology analysis which results in increased residence time of erythrocytes. Increasing the time available for counting these cells with semi-automated equipment thus allows groups of samples to be diluted and counted thereby increasing the efficiency of laboratory technicians.

A further objective of this invention is to provide a diluent which can be used for determining a single leukocyte population count as well as counts of sub-populations of leukocytes.

Another objective of this invention is to provide a diluent for use in obtaining sub-populations of leukocytes wherein the diluent employs an inorganic salt as the buffering agent. This significantly reduces the cost of the diluent in comparison with other suitable diluents for subpopulation analysis which have heretofore without exception employed expensive organic buffers.

Another objective of this invention is to provide a diluent for blood cell analysis which maintains the cellular morphology without utilization of cell stabilizing chemicals as has characterized various prior art diluents.

Another objective of this invention is to provide a diluent which can be used in cooperation with a lysing reagent to provide rapid and clean lysing without the necessity of additional chemicals.

Still another objective of this invention is to provide a diluent that meets all the objectives previously set forth and is also stable and bacteriostatic for long periods of time.

Other objectives of this invention will become apparent from a reading of the following description and claims.

DETAILED DESCRIPTION OF THE INVENTION

Although it was common practice to employ phosphate buffers in diluents and also to utilize sodium sulfate as a stabilizer in combination with procaine hydrochloride, it has been found that, when sodium sulfate is combined with sodium phosphate buffer, a superior diluent is obtained which results in a longer residence time of erythrocytes thus providing more time for counting and sizing of these cells. The diluent of this invention may also be utilized with completely automated equipment and is considerably less expensive than those utilizing organic buffers of the prior art which were thought to be necessary in order to obtain sub-populations of leukocytes. Also, expensive cell stabilizers are not required with the diluent of the instant invention.

Preparation of the diluent of the instant invention does not require special techniques and will be readily apparent to those skilled in the art. From 0.4-1.5% by weight of one or more of the group consisting of $Na_2SO_4$ and $NaNO_3$ is added to an aqueous solution together with 0.1-0.4% by weight of a salt of the formula $XH_2PO_4$ (hydrous or anhydrous) where X is either Na or K and 0.1-2.4% by weight of a salt of the formula $X_2HPO_4$ (hydrous or anhydrous) where X is Na or K. A mixture of Na and K phosphate salts may also be employed. The salts should be present in a ratio of from 1:1 (by weight) to 1:6, (by weight) $XH_2PO_4:X_2HPO_4$ and may be anhydrous or hydrous. The pH should be within the range of 6.0-8.0 with an osmotic strength of 200-400 milliosmoles. The sodium sulfate and/or sodium nitrate may be partially replaced by 0.01 to 1% by weight of one or more of the group comprising NaCl and KCl provided the sulfate and/or nitrate salt is present in a ratio of at least 1:1 relative to the chloride salt. In utilizing the diluent of the invention to prepare a whole blood sample for leukocyte determination, the whole blood sample is supplied along with a supply of the diluent of the formula set forth. The whole blood and the diluent are then mixed together. In semi-automated equipment, the mixture is then lysed manually with a lysing agent and the further diluted sample placed on the aperture assembly for counting of the leukocytes. In an automated system of the type disclosed in U.S. Pat. No. 3,549,994, the same steps are followed, but the mixture of whole blood and diluent remain in the lysing chamber where erythrocytes are stromatolysed automatically. The resulting suspension is then passed to a counting chamber where white blood cells are electronically sized and counted.

Various lysing solutions may be employed and are known to those skilled in the art. One suitable type of lyse is comprised of one or more quarternary ammonium salts having surface active properties as disclosed in U.S. Pat. No. 3,874,852. The lysing reagents are represented generally by the formula

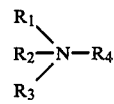

where $R_1$, $R_2$ and $R_3$ are a $C_1$ to $C_4$ alkyl and $R_4$ is a $C_{10}$ to $C_{20}$ alkyl. An alkali metal cyanide may also be used with the quaternary ammonium in solution for hemoglobin measurement. The lysing reagent will normally be used in a 1-6% by weight aqueous solution.

If leukocyte sub-populations are to be measured, it is necessary to employ one or more quarternary ammonium salts as the lysing agent in accordance with the teachings of U.S. Pat. No. 4,485,175. Suitable lysing agents include mixtures of dodecyltrimethylammonium chloride and tetradecyltrimethylammonium bromide or hexadecyltrimethylammonium bromide. The foregoing ammonium salts may be employed with an alkali metal cyanide for hemoglobin determinations.

A bacteriostat may also be employed in the diluent composition in a quantity of up to 0.5% by weight to inhibit the growth of bacteria. Examples of suitable bacteriostats include 1-hydroxypyridene-2-thione, 8-quinolinol, 8-quinolinol citrate, 8-hydroxyquinaldine (2-methyl-8-quinolinol), 8-hydroxyquinoline-5-sulfonic acid-dihydrate, and 8-hydroxy-5-nitroquinoline, and merthiolate.

A preferred formulation for the diluent of the invention is set forth in Example 1 below:

EXAMPLE 1

| % by weight | Component |
|---|---|
| 0.9 | $Na_2SO_4$ |
| 0.4 | NaCl |
| 0.04 | $NaH_2PO_4\ 2H_2O$ |
| 0.06 | $Na_2HPO_4$ |
| 0.001 | 1-hydroxypyridene-2-thione |
| 98.6 | $H_2O$ |

I claim:

1. A diluent for use in leukocyte analysis which maintains erythrocyte morphology consisting of an aqueous solution of:
   0.4 to 1.5% by weight of one or more of the group consisting of $Na_2SO_4$ and $NaNO_3$;
   0.01 to 0.4% by weight of a salt of the formula $XH_2PO_4$, hydrous or anhydrous, where X is either Na or K;
   0.01 to 0.6% by weight of a salt of the formula $X_2HPO_4$, hydrous or anhydrous, where X is either Na or K,
   said phosphate salts being present in a ratio of from 1:1 to 1:6 $XH_2PO_4:X_2HPO_4$; and
   0.01 to 1% by weight of one or both of NaCl and KCl, said member of the group consisting of $NaSO_4$ and $NaNO_3$ being present in a ratio of at least 1:1 (by weight) relative to the NaCl and KCl.

2. A method of preparing a whole blood sample for leukocyte determination while maintaining erythrocyte morphology comprising the steps of:
   supplying a whole blood sample;

supplying a diluent consisting of an aqueous solution of:
  0.4 to 1.5% by weight of one or more of the group consisting of $Na_2SO_4$ and $NaNO_3$;
  0.01 to 0.4% by weight of a salt of the formula $XH_2PO_4$, hydrous or anhydrous, where X is either Na or K;
  0.01 to 0.6% by weight of a salt of the formula $X_2HPO_4$, hydrous or anhydrous, where X is either Na or K,
  said phosphate salts being present in a ratio of from 1:1 to 1:6 (by weight) $XH_2PO_4:X_2HPO_4$,
  0.01 to 1% by weight of one or both of NaCl and KCl, said member of the group consisting of $NaSO_4$ and $NaNO_3$ being present in a ratio of at least 1:1 (by weight) relative to the NaCl and KCl;
mixing the whole blood and the diluent for a first analytical step; and
adding a lysing reagent to the diluted whole blood sample for subsequent analytical steps.

3. A method for determining the relative populations of at least the lymphocytes and granulocytes in a whole blood sample utilizing an automatic particle analyzing system, said method comprising the steps of:
supplying a whole blood sample to said system;
supplying a diluent for use in leukocyte analysis which maintains erythrocyte morphology consisting of an aqueous solution of:
  0.4 to 1.5% by weight of one or more of the group consisting of $Na_2SO_4$ and $NaNO_3$;
  0.01 to 0.4% by weight of a salt of the formula XH-hd 2PO4, hydrous or anhydrous, where X is either Na or K;
  0.01 to 0.6% by weight of a salt of the formula $X_2HPO_4$, hydrous or anhydrous, where X is either Na or K,
  said phosphate salts being present in a ratio of from 1:1 to 1:6 (by weight) $XH_2PO_4:X_2HPO_4$;
  0.01 to 1% by weight of one or both of NaCl and KCl, said member of the group consisting of $NaSO_4$ and $NaNO_3$ being present in a ratio of at least 1:1 (by weight) relative to the NaCl and KCl;
mixing the whole blood sample and the diluent for a first analytical step; and
mixing the whole blood sample and the diluent within the analyzing system with a lysing reagent thereby resulting in volumetric modification of the individual blood cells forming at least the lymphocyte and granulocyte subpopulations of leukocytes for a significant period of time to enable the automatic differentiation of these subpopulations by the analyzing system,
said lysing reagent comprising an aqueous solution of one or more quaternary ammonium salts.

4. A diluent for use in leukocyte analysis which maintains erythrocyte morphology consisting of an aqueous solution of:
  0.4 to 1.5% by weight of one or more of the group consisting of $Na_2SO_4$ and $NaNO_3$;
  0.01 to 0.4% by weight of a salt of the formula $XH_2PO_4$, hydrous or anhydrous, where X is either Na or K;
  0.01 to 0.6% by weight of a salt of the formula $X_2HPO_4$, hydrous or anhydrous, where X is either Na or K,
  said phosphate salts being present in a ratio of from 1:1 to 1:6 (by weight) $XH_2PO_4:X_2HPO_4$;
  0.01 to 1% by weight of one or both of NaCl and KCl, said member of the group consisting of $NaSO_4$ and $NaNO_3$ being present in a ration of at least 1:1 (by weight) relative to the NaCl and KCl; and
  a bacteria inhibiting effective quantity of a bacteriostat.

5. A diluent as set forth in claim 4 wherein said bacteriostat is present in a quantity of up to 0.5% by weight.

6. A diluent as set forth in claim 4 wherein said bacteriostat is selected from the group consisting of 1-hydroxypyridene-2-thione, 8-quinolinol, 8-quinolinol citrate, 8-hydroxyquinaldine (2-methyl-8-quinolinol), 8-hydroxyquinoline-5-sulfonic acid-dihydrate, and 8-hydroxy-5-nitroquinoline, and merthiolate.

7. A method of preparing a whole blood sample for leukocyte determination while maintaining erythrocyte morphology comprising the steps of:
supplying a whole blood sample;
supplying a diluent consisting of an aqueous solution of:
  0.4 to 1.5% by weight of one or more of the group consisting of $Na_2SO_4$ and $NaNO_3$;
  0.01 to 0.4% by weight of a salt of the formula $XH_2PO_4$, hydrous or anhydrous, where X is either Na or K;
  0.01 to 0.6% by weight of a salt of the formula $X_2HPO_4$, hydrous or anhydrous, where X is either Na or K,
  said phosphate salts being present in a ratio of from 1:1 to 1:6 (by weight) $XH_2PO_4:X_2HPO_4$,
  0.01 to 1% by weight of one or both of NaCl and KCl, said member of the group consisting of $NaSO_4$ and $NaNO_3$ being present in a ratio of at least 1:1 (by weight) relative to the NaCl and KCl;
  a bacteria inhibiting quantity of a bacteriostat;
mixing the whole blood and the diluent for a first analytical step; and
adding a lysing reagent to the diluted whole blood sample for subsequent analytical steps.

8. A method as set forth in claim 7, wherein said lysing reagent comprises a 1 to 6% by weight solution.

9. A method as set forth in claim 7 wherein said bacteriostat is selected from the group consisting of 1-hydroxypyridene-2-thione, 8-quinolinol, 8-quinolinol citrate, 8-hydroxyquinaldine (2-methyl-8-quinolinol), 8-hydroxyquinoline-5-sulfonic acid-dihydrate, and 8-hydroxy-5-nitroquinoline, and merthiolate.

10. A method for determining the relative populations of at least the lymphocytes and granulocytes in a whole blood sample utilizing an automatic particle analyzing system, said method comprising the steps of:
supplying a whole blood sample to said system;
supplying a diluent for use in leukocyte analysis which maintains erythrocyte morphology consisting of an aqueous solution of:
  0.4 to 1.5% by weight of one or more of the group consisting of $Na_2SO_4$ and $NaNO_3$;
  0.01 to 0.4% by weight of a salt of the formula $XH_2PO_4$, hydrous or anhydrous, where X is either Na or K;
  0.01 to 0.6% by weight of a salt of the formula $X_2HPO_4$, hydrous or anhydrous, where X is either Na or K.

said phosphate salts being present in a ratio of from 1:1 to 1:6 (by weight) $XH_2PO_4:X_2HPO_4$;

0.01 to 1% by weight of one or both of NaCl and KCl, said member of the group consisting of $NaSO_4$ and $NaNO_3$ being present in a ratio of at least 1:1 (by weight) relative to the NaCl and KCl;

a bacteria inhibiting quantity of a bacteriostat;

mixing the whole blood sample and the diluent for a first analytical step; and mixing the whole blood sample and the diluent within the analyzing system with a lysing reagent thereby resulting in volumetric modification of the individual blood cells forming at least the lymphocyte and granulocyte subpopulations of leukocytes for a significant period of time to enable the automatic differentiation of these subpopulations by the analyzing system, said lysing reagent comprising an aqueous solution of one or more quaternary ammonium salts.

11. A method as set forth in claim 10 wherein said bacteriostat is selected from the group consisting of 1-hydroxypyridene-2-thione, 8-quinolinol, 8-quinolinol citrate, 8-hydroxyquinaldine (2-methyl-8-quinolinol), 8-hydroxyquinoline-5-sulfonic acid-dihydrate, and 8-hydroxy-5-nitroquinoline, and merthiolate.

* * * * *

UNITED STATES PATENT AND TRADEMARK OFFICE
CERTIFICATE OF CORRECTION

PATENT NO. : 4,968,629
DATED : November 6, 1990
INVENTOR(S) : James D. Lapicola

It is certified that error appears in the above—identified patent and that said Letters Patent is hereby corrected as shown below:

In claim 3, at column 5, line 33, delete the formula

--XH-hd 2PO$_4$-- and insert in its place "XH$_2$PO$_4$".

Signed and Sealed this

Eighteenth Day of February, 1992

*Attest:*

HARRY F. MANBECK, JR.

*Attesting Officer*      *Commissioner of Patents and Trademarks*